US009375198B2

(12) United States Patent
Arts et al.

(10) Patent No.: US 9,375,198 B2
(45) Date of Patent: *Jun. 28, 2016

(54) METHODS AND SYSTEMS FOR ENHANCING ULTRASONIC VISIBILITY OF ENERGY-DELIVERY DEVICES WITHIN TISSUE

(71) Applicant: COVIDIEN LP, Mansfield, MA (US)

(72) Inventors: Gene H. Arts, Berthoud, CO (US);
Darion R. Peterson, Boulder, CO (US);
Joseph D. Brannan, Erie, CO (US);
John R. Vantuno, Broomfield, CO (US);
Eric W. Larson, Commerce City, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/747,597

(22) Filed: Jun. 23, 2015

(65) Prior Publication Data

US 2015/0289845 A1     Oct. 15, 2015

Related U.S. Application Data

(63) Continuation of application No. 13/836,353, filed on Mar. 15, 2013, now Pat. No. 9,066,681.

(60) Provisional application No. 61/664,555, filed on Jun. 26, 2012, provisional application No. 61/664,577, filed on Jun. 26, 2012, provisional application No. 61/664,559, filed on Jun. 26, 2012.

(51) Int. Cl.
*A61B 18/04*     (2006.01)
*A61B 8/08*      (2006.01)

(Continued)

(52) U.S. Cl.
CPC ............... *A61B 8/481* (2013.01); *A61B 8/0841* (2013.01); *A61B 18/1477* (2013.01);
(Continued)

(58) Field of Classification Search
CPC .. A61B 8/481; A61B 8/0841; A61B 18/1477; A61B 18/1482
See application file for complete search history.

(56) References Cited

U.S. PATENT DOCUMENTS

D223,367 S     4/1972 Kountz
D263,020 S     2/1982 Rau, III (Continued)

FOREIGN PATENT DOCUMENTS

CN     1103807 A    6/1995
DE      390937 C    3/1924

(Continued)

OTHER PUBLICATIONS

Paul G. Horgan, "A Novel Technique for Parenchymal Division During Hepatectomy" The American Journal of Surgery, vol. 181, No. 3, Apr. 2001, pp. 236-237.

(Continued)

*Primary Examiner* — Robert N Wieland

(57) ABSTRACT

Electrosurgical systems generally include at least one energy-delivery device for delivering energy to tissue when inserted or embedded within tissue. The energy-delivery device can be a tissue ablation device, such as an ablation probe, needle, etc. for ablating tissue as commonly known in the art. The electrosurgical systems include at least one structure and/or operational characteristic for enhancing ultrasonic visibility of the energy-delivery devices within tissue during ultrasonography.

10 Claims, 6 Drawing Sheets

(51) Int. Cl.
*A61B 18/14* (2006.01)
*A61B 18/18* (2006.01)
*A61B 18/00* (2006.01)
*A61B 17/34* (2006.01)
*A61B 17/00* (2006.01)

(52) U.S. Cl.
CPC ........ *A61B 18/1482* (2013.01); *A61B 18/1492* (2013.01); *A61B 18/1815* (2013.01); *A61B 2017/00084* (2013.01); *A61B 2017/00398* (2013.01); *A61B 2017/00539* (2013.01); *A61B 2017/3413* (2013.01); *A61B 2018/00023* (2013.01); *A61B 2018/00577* (2013.01); *A61B 2018/00642* (2013.01); *A61B 2018/00994* (2013.01); *A61B 2018/1861* (2013.01); *A61B 2018/1869* (2013.01); *A61B 2562/0219* (2013.01)

(56) References Cited

U.S. PATENT DOCUMENTS

| | | | |
|---|---|---|---|
| D266,842 S | 11/1982 | Villers et al. | |
| D278,306 S | 4/1985 | McIntosh | |
| 4,608,977 A | 9/1986 | Brown | |
| D295,893 S | 5/1988 | Sharkany et al. | |
| D295,894 S | 5/1988 | Sharkany et al. | |
| 4,869,259 A | 9/1989 | Elkins | |
| 4,977,897 A | 12/1990 | Hurwitz | |
| 5,000,185 A | 3/1991 | Yock | |
| 5,010,886 A | 4/1991 | Passafaro et al. | |
| 5,048,530 A | 9/1991 | Hurwitz | |
| 5,081,997 A | 1/1992 | Bosley, Jr. et al. | |
| 5,213,569 A | 5/1993 | Davis | |
| 5,221,269 A | 6/1993 | Miller et al. | |
| D354,218 S | 1/1995 | Van de Peer | |
| 5,383,466 A | 1/1995 | Partika | |
| 5,490,521 A | 2/1996 | Davis et al. | |
| 5,571,088 A | 11/1996 | Lennox et al. | |
| 5,611,345 A | 3/1997 | Hibbeln | |
| 5,630,837 A | 5/1997 | Crowley | |
| 5,766,135 A | 6/1998 | Terwilliger | |
| 5,769,795 A | 6/1998 | Terwilliger | |
| 6,053,870 A | 4/2000 | Fulton, III | |
| D424,693 S | 5/2000 | Pruter | |
| D424,694 S | 5/2000 | Tetzlaff et al. | |
| D425,201 S | 5/2000 | Tetzlaff et al. | |
| 6,241,725 B1 | 6/2001 | Cosman | |
| D449,886 S | 10/2001 | Tetzlaff et al. | |
| D457,958 S | 5/2002 | Dycus et al. | |
| D457,959 S | 5/2002 | Tetzlaff et al. | |
| 6,575,969 B1 | 6/2003 | Rittman, III et al. | |
| D487,039 S | 2/2004 | Webster et al. | |
| D496,997 S | 10/2004 | Dycus et al. | |
| D499,181 S | 11/2004 | Dycus et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| D564,662 S | 3/2008 | Moses et al. | |
| D576,932 S | 9/2008 | Strehler | |
| 7,488,289 B2 | 2/2009 | Suorsa et al. | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| 7,874,986 B2 | 1/2011 | Deckman et al. | |
| 7,879,031 B2 | 2/2011 | Peterson | |
| D634,010 S | 3/2011 | DeCarlo | |
| 8,206,300 B2 | 6/2012 | Deckman et al. | |
| 9,066,681 B2 | 6/2015 | Arts et al. | |
| 2002/0183742 A1 | 12/2002 | Carmel et al. | |
| 2003/0135117 A1 | 7/2003 | Ward et al. | |
| 2004/0158150 A1 | 8/2004 | Rabiner et al. | |
| 2004/0230111 A1 | 11/2004 | Smith et al. | |
| 2006/0058680 A1 | 3/2006 | Solomon | |
| 2007/0197954 A1* | 8/2007 | Keenan | A61B 8/0833 604/20 |
| 2008/0033417 A1 | 2/2008 | Nields et al. | |
| 2009/0118727 A1 | 5/2009 | Pearson et al. | |
| 2009/0292204 A1 | 11/2009 | Pansky | |
| 2009/0318804 A1 | 12/2009 | Avital et al. | |
| 2009/0326529 A1 | 12/2009 | Brace et al. | |
| 2010/0286528 A1 | 11/2010 | Davis et al. | |
| 2013/0116683 A1* | 5/2013 | Shadduck | A61B 18/04 606/41 |
| 2013/0158390 A1 | 6/2013 | Tan et al. | |
| 2013/0261454 A1 | 10/2013 | Hennings et al. | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10217281 A1 | 10/2003 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102008054083 A1 | 5/2010 |
| DE | 102009015699 A1 | 5/2010 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1159926 A3 | 3/2003 |
| FR | 179 607 | 11/1906 |
| FR | 1 275 415 A | 11/1961 |
| FR | 1 347 865 A | 2/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |

(56) References Cited

FOREIGN PATENT DOCUMENTS

| | | |
|---|---|---|
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2008142467 A | 6/2008 |
| SU | 166452 | 1/1965 |
| SU | 401367 A1 | 10/1973 |
| SU | 727201 A2 | 4/1980 |
| WO | 00/36985 A2 | 6/2000 |
| WO | 2010/035831 A1 | 4/2010 |

OTHER PUBLICATIONS

Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.

Urologix, Inc.-Medical Professionals: Targis.TM. Technology, "Overcoming the Challenge" located at: <http://www.urologix.com-!medicaUtechnology.html>Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Examination Report dated Mar. 9, 2015, corresponding to European Patent Application No. 13171825.6; 5 pages.
Extended European Search Report corresponding to EP 13 17 1825, dated Nov. 13, 2013; 8 pages.
U.S. Appl. No. 08/136,098, filed Oct. 14, 1993, Roger A. Stern.
U.S. Appl. No. 08/483,742, filed Jun. 7, 1995 Roger A. Stern.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/343,788, filed Jan. 5, 2012, William O. Reid, Jr.
U.S. Appl. No. 13/343,798, filed Jan. 5, 2012, William O. Reid, Jr.
U.S. Appl. No. 13/344,753, filed Jan. 6, 2012, Lee et al.
U.S. Appl. No. 13/344,790, filed Jan. 6, 2012, Lee et al.
U.S. Appl. No. 13/358,129, filed Jan. 25, 2012, Brannan.
U.S. Appl. No. 13/400,223, filed Feb. 20, 2012, Anthony B. Ross.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/657,270, filed Oct. 22, 2012, Brannan.
U.S. Appl. No. 13/657,609, filed Oct. 22, 2012, Prakash.
U.S. Appl. No. 13/657,638, filed Oct. 22, 2012, Brannan.
U.S. Appl. No. 13/681,741, Nov. 20, 2012, Steven Kim.
U.S. Appl. No. 13/711,067, filed Dec. 11, 2012, Brannan.
U.S. Appl. No. 13/711,086, filed Dec. 11, 2012, Brannan.
U.S. Appl. No. 13/711,164, filed Dec. 11, 2012, Brannan.
U.S. Appl. No. 13/734,638, filed Jan. 4, 2013, Bonn.
U.S. Appl. No. 13/740,706, filed Jan. 14, 2013, Rossetto.
U.S. Appl. No. 13/740,754, filed Jan. 14, 2013, Prakash.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.

(56) References Cited

OTHER PUBLICATIONS

Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.

Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman et al., "Laparoscopic Intestinal Resection With the LigaSure. TM. Vessel Sealing System: A Case Report" Innovations That Work, Feb. 2002.
Humphries Jr. et al., "Finite.cndot.Element Codes to Model Electrical Heating and Non.cndot.L1near Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.

(56) References Cited

OTHER PUBLICATIONS

MDTech product literature (Dec. 1999) "FlexStrand": product description, 1 page.
MDTech product literature (Mar. 2000) I'd Wire: product description, 1 page.
Medtrex Brochure "The O.R. Pro 300" 1 page, Sep. 1998.
Michael Choti, "Abdominoperineal Resection with the LigaSure.TM. Vessel Sealing System and LigaSure.TM. Atlas 20 cm Open Instrument" Innovations That Work, Jun. 2003.
Muller et al., "Extended Left Hemicolectomy Using the LigaSure.TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences. cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.

\* cited by examiner

METHODS AND SYSTEMS FOR ENHANCING ULTRASONIC VISIBILITY OF ENERGY-DELIVERY DEVICES WITHIN TISSUE

CROSS REFERENCE TO RELATED APPLICATION

The present application is a continuation of U.S. patent application Ser. No. 13/836,353, filed on Mar. 15, 2013, now U.S. Pat. No. 9,066,681, which claims the benefit of and priority to U.S. Provisional Application Ser. No. 61/664,555, filed on Jun. 26, 2012, U.S. Provisional Application Ser. No. 61/664,577, filed on Jun. 26, 2012, and U.S. Provisional Application Ser. No. 61/664,559, filed on Jun. 26, 2012, the entire contents of each of which are incorporated herein by reference.

BACKGROUND

1. Technical Field

The present disclosure relates to electrosurgical devices suitable for tissue ablation applications and, more particularly, to methods and systems for enhancing ultrasonic visibility of energy-delivery devices within tissue.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

There are several types of microwave probes in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly-aligned and positioned end-to-end relative to one another with an electrical insulator placed therebetween. Helical antenna assemblies include helically-shaped conductor configurations of various dimensions, e.g., diameter and length. The main modes of operation of a helical antenna assembly are normal mode (broadside), in which the field radiated by the helix is maximum in a perpendicular plane to the helix axis, and axial mode (end fire), in which maximum radiation is along the helix axis.

During certain procedures, a probe may be inserted directly into tissue, inserted through a lumen, e.g., a vein, needle or catheter, or placed into the body using surgical techniques. Multiple probes may be used to synergistically create a large ablation or to ablate separate sites simultaneously.

Ultrasonography or computed tomography (CT) guidance may used prior to ablation treatments for aiding probe placement. Ultrasonography is the imaging of deep structures in the body by recording the echoes of pulses of high frequency ultrasonic or sound waves directed into tissue and reflected by tissue planes where there is a change in density. A change in density exists along the plane or boundary between two types of tissue or between tissue and a non-anatomical structure, such as an energy-delivery device, such as, for example, an ablation probe within the tissue. Due to different acoustic impedances among the different types of anatomical structures, and non-anatomical structures within tissue, ultrasonography produces visual images of the anatomical and non-anatomical structures within the body.

However, during certain surgical procedures, it can be difficult to visualize an ablation probe, needle, catheter, etc. within the body using ultrasonography. As a result, it is difficult to guide surgical instruments to a proper location and/or position within the body, such as, for example, an ablation probe within a tissue mass to be ablated. Hence, techniques and improvements are needed to enhance the visualization of surgical instruments, especially, energy delivery devices, within tissue during ultrasonography.

SUMMARY

Various embodiments of the present disclosure provide methods and systems for enhancing ultrasonic visibility of energy-delivery devices. As used herein, the term "distal" refers to the portion that is being described which is further from a user, while the term "proximal" refers to the portion that is being described which is closer to a user. Further, to the extent consistent with one another, any of the aspects described herein may be used in conjunction with any of the other aspects described herein.

The term "ultrasonic visibility" is defined herein as the amount an object within tissue is visible or distinguishable from surrounding tissue during ultrasonography. The term "energy-delivery device" is defined herein to include any surgical instrument, device or apparatus capable of delivering energy to tissue, including, but not limited to, radiofrequency and microwave energy. Even though the present disclosure describes enhancing the ultrasonic visibility of an energy-delivery device, one skilled in the art can embody the novel aspects described herein to enhance the ultrasonic visibility of other devices which are inserted, implanted, guided, positioned, etc. within tissue, such as, for example, surgical patches, stents, metal rods, spinal implants, artificial joints, etc.

In accordance with aspects of the present disclosure, electrosurgical systems are provided generally including at least one energy-delivery device for delivering energy to tissue when inserted or embedded within tissue. The energy-delivery device can be a tissue ablation device, such as an ablation probe, needle, etc. for ablating tissue as commonly known in the art. The electrosurgical systems include at least one structure and/or operational characteristic for enhancing ultrasonic visibility of the energy-delivery devices within tissue during ultrasonography.

According to the present disclosure, different aspects are disclosed for enhancing the ultrasonic visibility of at least one structure of the energy-delivery device, such as an ablation probe, during ultrasonography, which, in turn, aids in the positioning and placement of the energy-delivery device within tissue. The at least one structure can include, but not limited to, a shaft extending from a handle assembly or hub, an ablation probe, an ablation needle, a trocar at a distal end of an ablation probe, and a cooling jacket.

In one aspect of the present disclosure, ultrasonic visibility of the energy-delivery device, such as an ablation probe, within tissue is enhanced by mechanical vibration. According to this aspect of the present disclosure, an electrosurgical system is provided capable of performing tissue ablation. The electrosurgical system includes a handle assembly, an energy-delivery device at least partially housed within a shaft and extending from the handle assembly, and a high-speed motor. The electrosurgical system further includes controls for activating the energy-delivery device and the motor. The motor can be powered by a battery or by a generator powering the electrosurgical system. The electrosurgical system can also include controls for actuating a pump, such as a peristaltic pump, for circulating cooling fluid through the energy-delivery device. The controls can be provided on the handle assembly.

The motor is positioned within the handle assembly at a proximal end of the energy-delivery device. The motor is in operative mechanical communication via a mechanical linkage assembly with a weight, such as an eccentric weight, positioned inside the energy-delivery device at a distal end thereof.

During placement of the energy-delivery device within tissue or at anytime when enhanced ultrasonic visibility of the energy-delivery device within tissue is desired, the motor is actuated thereby causing vibration of the weight at the distal end of the energy-delivery device. The vibration of the weight causes the energy-delivery device to vibrate. The vibrating energy-delivery device enhances its ultrasonic visibility.

In a similar aspect of the present disclosure, the high speed motor is positioned on the handle assembly. A weight, such as an eccentric weight, is connected to the motor. When the motor is actuated, mechanical vibration energy is transferred or transmitted to the distal end of the energy-delivery device causing the energy-delivery device to vibrate. The vibrating energy-delivery device enhances its ultrasonic visibility.

Variations of the above described mechanical vibration aspects include at least one of adjusting the speed of the motor to determine the resonant frequency of the energy-delivery device, adjusting the speed of the motor to determine the harmonic frequency of the ultrasonic imaging system, and positioning the weight at a distal end of the energy-delivery device.

In still another aspect of the present disclosure, the electrosurgical system includes a controller, such as a processor, for performing at least two or more of the mechanical vibrating actions described above for vibrating the energy-delivery device, such as, for example, rapidly varying or sweeping the frequency to allow the energy-delivery device to continually pass through the resonant frequency of the energy-delivery device or harmonic frequency of the ultrasonic imaging system.

In similar aspects as those described above with respect to an electrosurgical system having a handle assembly, the electrosurgical system can be of the type having a hub, as opposed to a handle assembly, from which an energy-delivery device extends from. In such an electrosurgical system, the motor can be positioned on or within the hub for transferring mechanical vibration energy to the distal end of the energy-delivery device.

In another aspect of the present disclosure, ultrasonic visibility of the energy-delivery device within tissue is enhanced by hydraulic vibration. According to this aspect of the present disclosure, the energy-delivery device of the electrosurgical system can be caused to vibrate by circulating cooling fluid. In a similar aspect of the present disclosure, ultrasonic visibility of the energy-delivery device of the electrosurgical system is enhanced by selectively blocking the fluid flow of the cooling fluid. This causes high pressure pulses in the fluid flow. The high pressure pulses, in turn, cause vibration of the energy-delivery device which enhances the ultrasonic visibility of the energy-delivery device.

In still another similar aspect of the present disclosure, controls can be used to control the speed of the pump. At higher pumping speeds, the fluid pressure of the circulating cooling fluid through the energy-delivery device is increased, thereby causing increased vibration of the energy-delivery device. The speed of the pump can also be adjusted in similar aspects of the present disclosure to determine the resonant frequency of the energy-delivery device or the harmonic frequency of the ultrasonic imaging system.

In another aspect of the present disclosure, the electrosurgical system includes a pulsating device in operative communication with the pump. The pulsating device rapidly alternates the direction of fluid flow for achieving maximum hydraulic pressure change within the energy-delivery device and vibration of the energy-delivery device. The vibration of the energy-delivery device enhances the ultrasonic visibility of the energy-delivery device.

In still another aspect of the present disclosure, the electrosurgical system is capable of performing at least two or more of the hydraulic vibrating actions described above for vibrating the energy-delivery device, such as, for example, blocking the fluid flow while a controller, such as a processor, rapidly varies or sweeps the frequency to allow the energy-delivery device to continually pass through the resonant frequency (or harmonic frequency) of the ultrasonic imaging system.

In another aspect of the present disclosure, ultrasonic visibility of the energy-delivery device within tissue is enhanced by providing an air cavity at or near the distal end of the energy-delivery device, such as, for example, at or near the tip of an ablation probe, RF electrode or microwave antenna. The air cavity is created by creating a ring groove circumferentially around the energy-delivery device, such as, for example, circumferentially around an ablation probe, near the tip. The ring groove provides an air pocket. The air pocket can be created when heat shrink is placed over the top of the energy-delivery device. The air pocket enhances ultrasonic visibility of the energy-delivery device during placement, since air has a very high ultrasonic contrast compared to the surrounding tissue because of the difference in density and acoustic properties.

In still another aspect of the present disclosure, ultrasonic visibility of the energy-delivery device within tissue is enhanced by positioning a metal band to the energy-delivery device, such as, for example, positioning a metal band on a shaft or cooling jacket extending from a handle assembly, at a distal end of an ablation probe or needle, or between a trocar at a distal end of an ablation assembly and a cooling jacket. The metal band can be provided with small dimples to further enhance the ultrasonic visibility of the energy-delivery device.

In yet another aspect of the present disclosure, ultrasonic visibility of the energy-delivery device within tissue is enhanced by making the shape of a cooling jacket or shaft of the energy-delivery device multi-sided, such as, for example, making the outer surface of the energy-delivery device hexagonal. The cooling jacket or shaft can be made multi-sided at or near the region of the radiating section of the energy-delivery device, such as at or near the distal end of an ablation probe. The flat or substantially flat sides of the cooling jacket or shaft enhance the ultrasonic visibility of the energy-delivery device. The surface of at least one side can be made concave and/or be provided with small dimples for enhanced ultrasonic visibility of the energy-delivery device.

In another aspect of the present disclosure, ultrasonic visibility of the energy-delivery device within tissue is enhanced by wrapping the energy-delivery device with multiple metallic wires. The wires can be individual loops or wrapped in the form of a coil or spring. The wires are placed proximal to a radiating section of the energy-delivery device in order to aid in identifying the start of the radiating section without interfering with the emitted energy, such as microwave energy. The wires can also be placed over the active area of the radiating section in the case of an RF electrode, such as, a Cool-Tip™ electrode.

In yet another aspect of the present disclosure, ultrasonic visibility of the energy-delivery device within tissue is enhanced by adding fluid, such as a gel, liquid or gas, along an inner chamber of the shaft or within a sac or balloon positioned along the shaft. The inner chamber, sac or balloon can be inflated with the fluid, e.g., air, when ultrasonic visibility of the energy-delivery device is desired. In one configuration, the fluid is added between a cooling jacket and an outermost heat shrink, such as a PET heat shrink, during ultrasonography. If a liquid is used as the fluid, the ultrasonic energy is absorbed and the liquid appears darker in contrast compared to surrounding tissue. If air is used as the fluid, the ultrasonic energy is reflected and the air appears brighter in contrast compared to surrounding tissue. The fluid can be added during guidance, positioning and placement of the energy-delivery device within tissue, and be removed during the ablation procedure. The sac or balloon can be positioned in the area proximal to a radiating section or on the radiating section of the energy-delivery device.

In another aspect of the present disclosure, ultrasonic visibility of the energy-delivery device within tissue is enhanced by increasing ultrasound reflection at or near the distal end of the energy-delivery device, such as, for example, at a trocar. The ultrasound reflection is increased by creating a concave surface at the distal end and/or adding a plurality of dimples to the surface of the distal end. Ultrasonic visibility is also increased by making the trocar multi-sided.

The distal end can be made from ceramic material which is molded to have a concave surface and/or a plurality of dimples thereon. The concave surface and/or plurality of dimples increase the amount of ultrasonic energy which is reflected by the energy-delivery device, thereby enhancing its ultrasonic visibility. The dimples can also be added on a cooling jacket, shaft, heat shrink or other structure of the energy-delivery device.

In another aspect of the present disclosure, ultrasonic visibility of the energy-delivery device within tissue is enhanced by releasing bubbles in proximity to the radiating section or a distal end of the energy-delivery device. The bubbles increase ultrasound reflection at or near the distal end of the energy-delivery device. The bubbles can be produced through electrolysis using an anode and cathode arrangement.

Finally, in yet another aspect of the present disclosure, ultrasonic visibility of the energy-delivery device within tissue is enhanced by adding micro spheres or protrusions of a hard material, such as, ceramic, glass, stainless steel, etc., at or near the radiating section or a distal end of the energy-delivery device. The micro spheres or protrusions can also be added on a cooling jacket, shaft, heat shrink or other structure of the energy-delivery device.

According to the above aspects, the present disclosure provides an electrosurgical system which includes an energy-delivery device adapted to direct energy to tissue. The system further includes a vibrating device in mechanical communication with the energy-delivery device for transmitting vibrational energy to the energy-delivery device when the vibrating device is actuated. The vibrational energy causes the energy-delivery device to vibrate. The electrosurgical system further includes a weight connected to the vibrating device, such as an eccentric weight. The energy-delivery device is selected from the group consisting of an electrode, a probe, and an antenna.

The electrosurgical system further includes a hub connected to the energy-delivery device. The vibrating device can be positioned with the hub. The vibrating device is a motor.

The electrosurgical system further includes controls or a controller, such as a processor, for at least one of adjusting the speed of the vibrating device to determine a resonant frequency of the energy-delivery device, and adjusting the speed of the vibrating device to determine a harmonic frequency of an ultrasonic imaging system in operative communication with the electrosurgical system. The controller can also sweep the frequency of the vibrating device. At least one accelerometer is positioned at a distal end of the energy-delivery device.

The electrosurgical system further includes an assembly in fluid communication with a distal end of the energy-delivery device for delivering fluid to the distal end. The assembly enables bubbles to be released from the distal end.

The energy-delivery device includes an air cavity defined therein. The energy-delivery device can further include a metal band.

The energy-delivery device includes a wire wrapped around an outer surface of the energy-delivery device. The outer surface of the energy-delivery device can be multi-sided. The distal end of the energy-delivery device can include at least one of a plurality of dimples and a plurality of protrusions. The distal end of the energy-delivery device can include a concave surface.

The present disclosure also provides a method for increasing the ultrasonic visibility of an energy-delivery device of an electrosurgical system within tissue. The method includes providing the electrosurgical system with a vibrating device in mechanical communication with the energy-delivery device. The method also includes actuating the vibrating device for transmitting vibrational energy to the energy-delivery device during ultrasonography. The vibrational energy causes the energy-delivery device to vibrate, and thereby increasing the ultrasonic visibility of the energy-delivery device.

The method further includes positioning the vibrating device with a handle assembly of the electrosurgical system.

The method further includes at least one of adjusting the speed of the vibrating device to determine a resonant frequency of the energy-delivery device, and adjusting the speed of the vibrating device to determine a harmonic frequency of an ultrasonic imaging system in operative communication with the electrosurgical system. The method can further include sweeping the frequency of the vibrating device.

In additional embodiment according to the present disclosure, an electrosurgical system is provided which includes an energy-delivery device adapted to direct energy to tissue; and a metal band positioned on the energy-delivery device. The metal band can be fixedly or removably positioned on the energy-delivery device. The metal band includes a plurality of dimples. The energy-delivery device is selected from the group consisting of an electrode, a probe, and an antenna.

In a further additional embodiment according to the present disclosure, an electrosurgical system is provided which includes an energy-delivery device adapted to direct energy to tissue. The energy-delivery device defines an air cavity at a distal end thereof. The energy-delivery device can be a probe having a trocar at the distal end, and wherein the air cavity is defined proximally to the trocar. The energy-delivery device is selected from the group consisting of an electrode, a probe, and an antenna.

An electrosurgical system is also provided according to another embodiment of the present disclosure which includes an energy-delivery device adapted to direct energy to tissue; and a balloon assembly having an inflatable balloon positioned on the energy-delivery device and at least one conduit in fluid communication with a fluid source for delivering and withdrawing fluid to the balloon for selectively inflating and deflating the balloon. The energy-delivery device is selected from the group consisting of an electrode, a probe, and an antenna.

An electrosurgical system is also provided according to another embodiment of the present disclosure which includes an energy-delivery device adapted to direct energy to tissue; and a hydraulic assembly. The hydraulic assembly includes a fluid source in fluid communication with a distal end of the energy-delivery device. The hydraulic assembly further includes a flow-control device for selectively blocking and unblocking fluid flow, or controlling the rate of fluid flow. The hydraulic assembly creates and transmits hydraulic energy to the energy-delivery device for vibrating the energy-delivery device. The flow-control device can be a valve. The energy-delivery device is selected from the group consisting of an electrode, a probe, and an antenna.

The electrosurgical system further includes a pulsating device in operative communication with the flow-control device. The pulsating device alternates the direction of fluid flow.

The present disclosure further includes a method according to another embodiment for increasing the ultrasonic visibility of an energy-delivery device of an electrosurgical system within tissue during ultrasonography. The method includes providing the electrosurgical system with a hydraulic assembly in fluid communication with a distal end of the energy-delivery device and a flow-control device. The method also includes controlling the flow-control device for selectively blocking and unblocking fluid flow, or controlling the rate of fluid flow, for creating and transmitting hydraulic energy to the energy-delivery device for vibrating the energy-delivery device. The flow-control device can be a valve or a pump. The energy-delivery device is selected from the group consisting of an electrode, a probe, and an antenna.

The controlling step includes varying the speed of the flow-control device to selectively adjust the rate of the fluid flow. The controlling step creates and transmits the hydraulic energy in the form of high pressure pulses to the energy-delivery device. The controlling step is performed by a processor unit. The controlling step includes controlling the amount of time the fluid flow is blocked. The controlling step further includes controlling the rate of the fluid flow. The controlling step also includes controlling the flow-control device using temperature data received from at least one temperature sensor.

The method further includes positioning the flow-control device on the energy-delivery device. The method also includes utilizing the hydraulic assembly for cooling the energy-delivery device. Additionally, the method includes adjusting the speed of the flow-control device to determine the resonant frequency of the energy-delivery device or the harmonic frequency of an ultrasonic imaging system performing the ultrasonography.

The method also includes alternating the direction of fluid flow. Additionally, the method includes sweeping the frequency to allow the energy-delivery device to pass through the resonant frequency or harmonic frequency of the ultrasonic imaging system performing the ultrasonography.

BRIEF DESCRIPTION OF THE DRAWINGS

Objects and features of the presently-disclosed to methods and systems for enhancing ultrasonic visibility of energy-delivery devices within tissue will become apparent to those of ordinary skill in the art when descriptions of various embodiments thereof are read with reference to the accompanying drawings, of which.

DETAILED DESCRIPTION

Figure 1A:
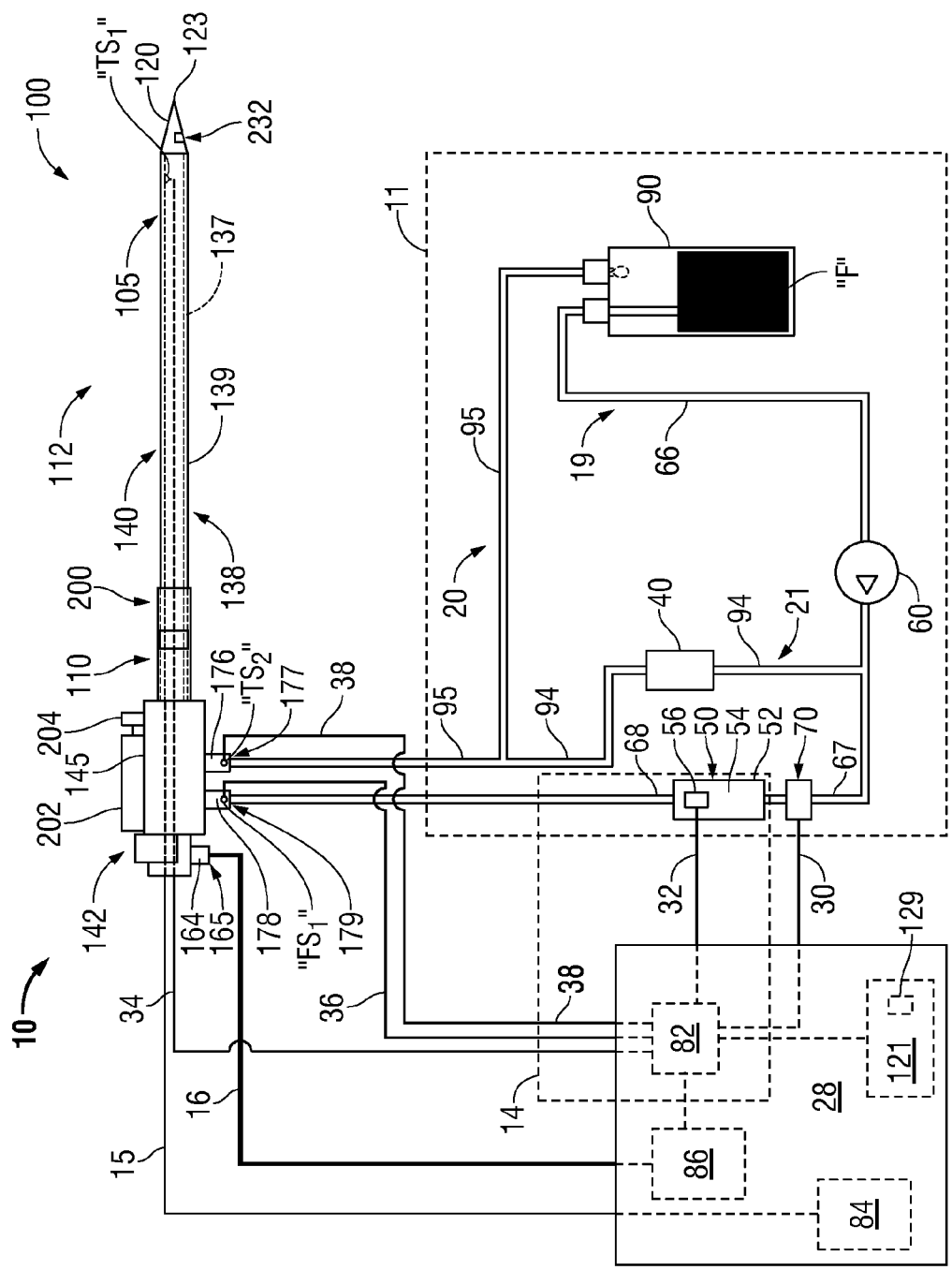
FIG. 1A is a schematic diagram of an electrosurgical system having an energy-delivery device and a vibrating device positioned on a hub in accordance with an embodiment of the present disclosure.

Hereinafter, embodiments of the presently-disclosed methods and systems for enhancing ultrasonic visibility of energy-delivery devices (or other component) of an electrosurgical system within tissue are described with reference to the accompanying drawings. Like reference numerals may refer to similar or identical elements throughout the description of the figures.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

In accordance with the present disclosure, electrosurgical systems are provided generally including at least one energy-delivery device for delivering energy to tissue when inserted or embedded within tissue. The electrosurgical systems include at least one structure and/or operational characteristic for enhancing ultrasonic visibility of the energy-delivery devices within tissue during ultrasonography.

Enhancing the ultrasonic visibility of the energy-delivery device using an ultrasonic imaging system is beneficial for aiding in the placement of the energy-delivery devices during percutaneous and surgical procedures. This is because there is very little ultrasonic contrast between the tissue and energy-delivery devices which makes it difficult to distinguish energy-delivery devices as they pass through the tissue.

The energy-delivery device can be a tissue ablation device, such as an ablation probe, needle, etc. for ablating tissue as commonly known in the art. The ablation probe, for exemplary purposes in describing the various embodiments of the present disclosure, is an ablation probe including a fluid-cooled antenna assembly.

Additionally, the electrosurgical system described herein for exemplary purposes includes a thermal-feedback that controls the rate of fluid flow to the ablation probe. It is contemplated that embodiments of the present disclosure for enhancing ultrasonic visibility of energy-delivery devices or other components of the electrosurgical system within tissue can be implemented, integrated and/or otherwise incorporated in other systems and energy-delivery devices which are not described or mentioned herein. The description of the embodiments of the present disclosure to certain systems, especially electrosurgical systems, is for exemplary purposes only and shall not be construed as limiting the embodiments described herein to only these systems and variants thereof. That is, for example, embodiments may be implemented using electromagnetic radiation at microwave frequencies or at other frequencies.

According to various embodiments, the electrosurgical system is designed and configured to operate between about 300 MHz and about 10 GHz. Systems for enhancing ultrasonic visibility of an energy-delivery device, as described herein, may be used in conjunction with various types of devices, such as microwave antenna assemblies having either a straight or looped radiating antenna portion, etc., which may be inserted into tissue to be treated.

Various embodiments of the presently-disclosed electrosurgical systems utilizing methods and systems for enhancing ultrasonic visibility of an energy-delivery device are suitable for microwave ablation and for use to pre-coagulate tissue for microwave ablation-assisted surgical resection. Although various methods and systems described herein below are targeted toward ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue.

FIG. 1A shows an electrosurgical system 10 according to an embodiment of the present disclosure that includes an energy-delivery device in the form of an ablation probe 100, an electrosurgical power generating source 28, e.g., a microwave or RF electrosurgical generator, and an electrolysis assembly 84 in fluid communication with a distal end of the energy-delivery device 100. The electrolysis assembly 84 enables the generation and release of bubbles at a distal end of the ablation probe 100 for enhancing ultrasonic visibility according to one embodiment of the present disclosure.

The bubbles are produced by the electrolysis assembly 84 through electrolysis using an anode and cathode arrangement. The bubbles enhance the ultrasonic visibility of the ablation probe 100 during ultrasonography. The bubbles reflect ultrasonic energy delivered by an ultrasonic generator during ultrasonography making them brighter in contrast compared to surrounding tissue and the ablation probe. Accordingly, by noticing the brighter contrast, one can determine the location and position of the distal end of the ablation probe 100 within tissue.

The electrosurgical system 10 further includes a feedback control system 14 operably associated with a coolant supply system 11. Probe 100 is operably coupled to the electrosurgical power generating source 28, and disposed in fluid communication with the coolant supply system 11.

In some embodiments, one or more components of the coolant supply system 11 may be integrated fully or partially into the electrosurgical power generating source 28. Coolant supply system 11, which is described in more detail later in this description, is adapted to provide coolant fluid "F" to the probe 100. Probe 100, which is described in more detail later in this description, may be integrally associated with a hub 142 configured to provide electrical and/or coolant connections to the probe 100.

In some embodiments, the electrosurgical system 10 includes one or more sensors capable of generating a signal indicative of a temperature of a medium in contact therewith (referred to herein as temperature sensors) and/or one or more sensors capable of generating a signal indicative of a rate of fluid flow (referred to herein as flow sensors). In such embodiments, the feedback control system 14 may be adapted to provide a thermal-feedback-controlled rate of fluid flow to the probe 100 using one or more signals output from one or more temperature sensors and/or one or more flow sensors operably associated with the probe 100 and/or conduit fluidly-coupled to the probe 100.

The probe 100 as shown by FIG. 1A includes a strain relief 200. The strain relief 200 is fixed to a surface of the hub 142 to counter mechanical stress when the probe 100 bends during an electrosurgical procedure. In some embodiments, the probe 100 may extend from a handle assembly as shown by several of the figures.

Figure 1B:
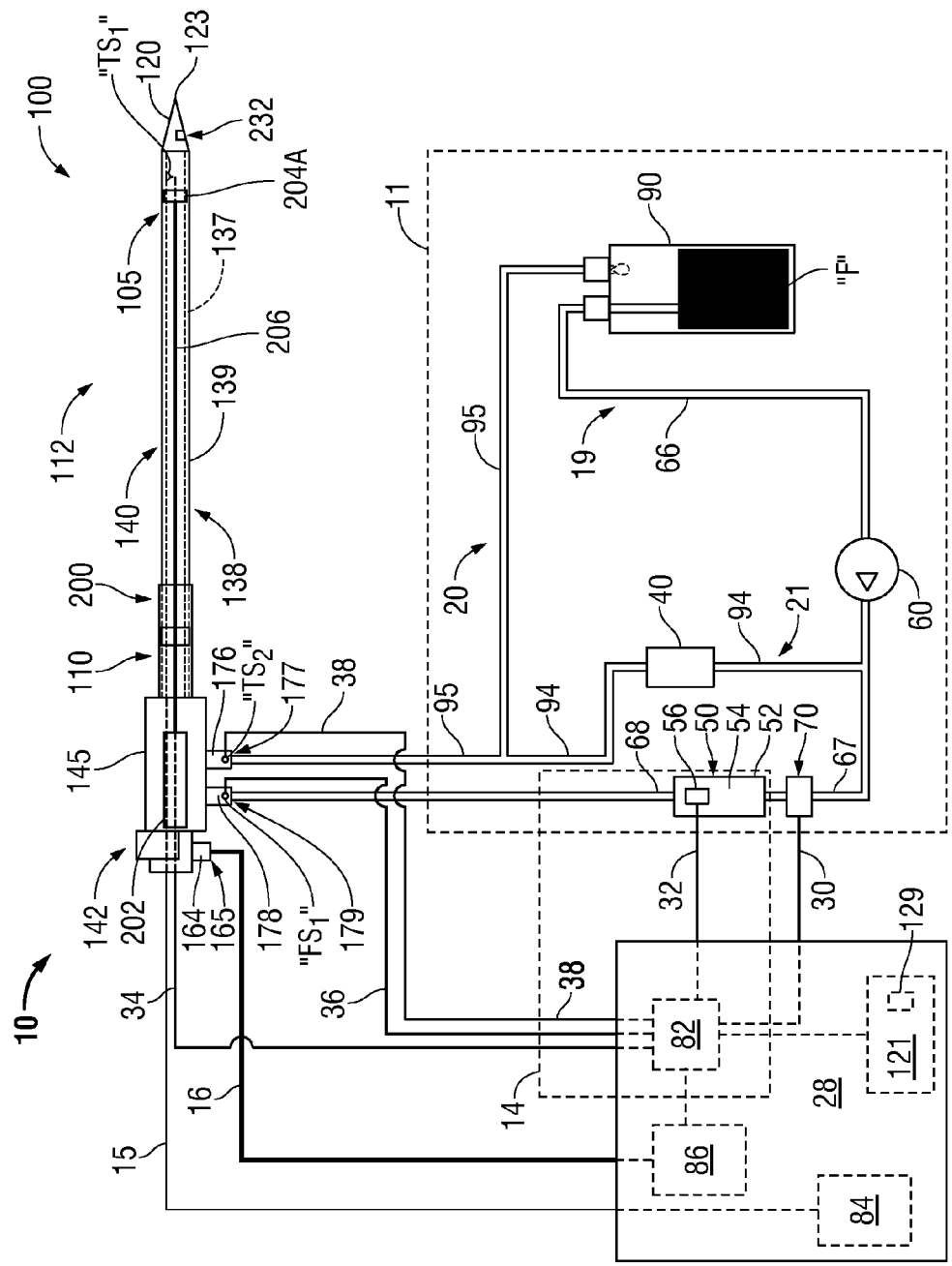
FIG. 1B is a schematic diagram of an electrosurgical system having an energy-delivery device and a vibrating device positioned within a hub in accordance with an embodiment of the present disclosure.

In embodiments according to the present disclosure, as shown by FIGS. 1A and 1B, ultrasonic visibility of the energy-delivery device, such as the ablation probe 100, within tissue is enhanced by mechanical vibration. The electrosurgical system 10 of FIG. 1A is provided with a motor 202. The motor 202 is positioned on hub 142 from which the ablation probe 100 extends from. The motor 202 can include an eccentric weight 204. The motor 202 and eccentric weight 204 cause mechanical vibration energy to be transferred or transmitted from the proximal end of the ablation probe 100 to the distal end of the ablation probe 100 when the motor 202 is actuated. The mechanical vibration energy causes ablation probe 100, including its distal end, to vibrate. A vibrating distal end of the ablation probe 100 has greater ultrasonic visibility than a non-vibrating distal end.

The motor 202 can also be positioned inside the hub 142 as shown by FIG. 1B. When the motor 202 is positioned within the hub 142, an eccentric weight 204A can be provided at a distal end of the ablation probe 100. The eccentric weight 204A is mechanically connected to the motor 202 via a mechanical linkage assembly 206, such as a rigid rod, designed to transfer mechanical vibration energy from the motor 202 to the eccentric weight 204A. The mechanical vibration energy causes the eccentric weight 204A at the distal end of the probe 100 to vibrate, and thereby impart vibrational energy to the distal end of the ablation probe 100. The vibrational energy causes the ablation probe 100, especially its distal end, to vibrate, and thereby increase the ultrasonic visibility of the probe 100.

Figure 2:
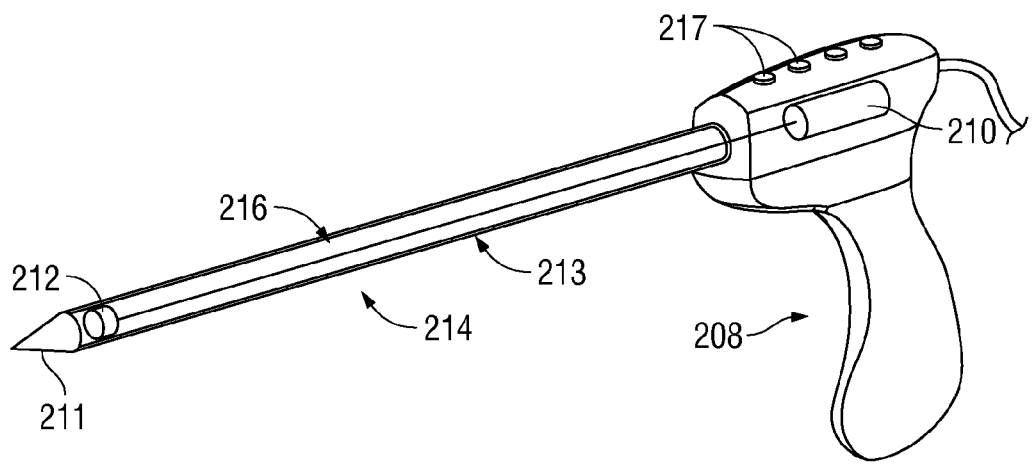
FIG. 2 is a schematic diagram of an electrosurgical system having a handle assembly and a vibrating device positioned within the handle assembly in accordance with an embodiment of the present disclosure.
Figure 3:
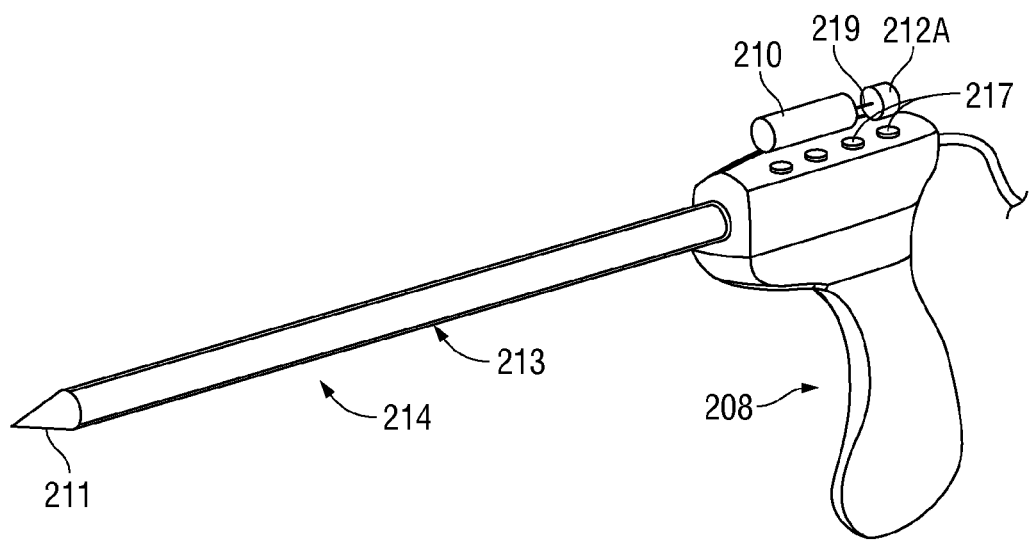
FIG. 3 is a schematic diagram of an electrosurgical system having a handle assembly and a vibrating device positioned on the handle assembly in accordance with an embodiment of the present disclosure.
Figure 4:
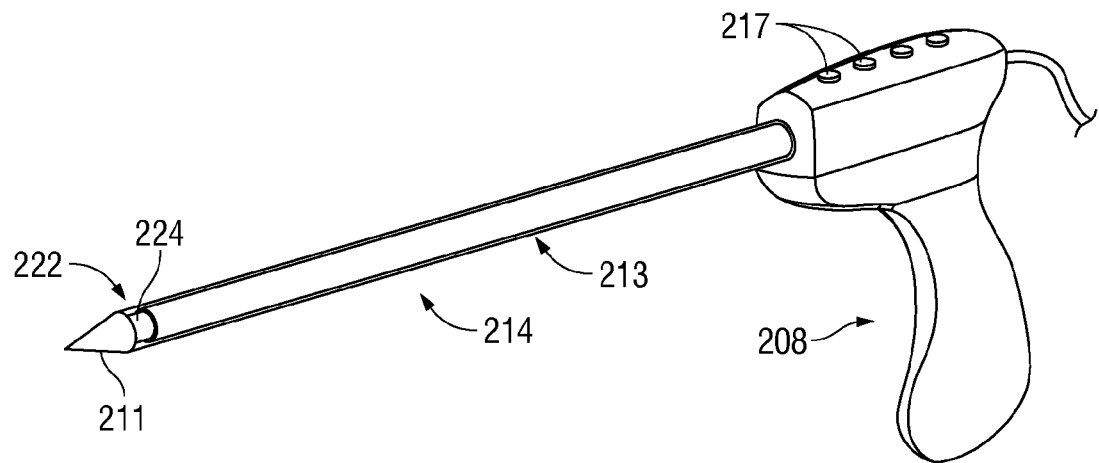
FIG. 4 is a schematic diagram of an electrosurgical system having a handle assembly and an energy-delivery device defining an air cavity in accordance with an embodiment of the present disclosure.

FIGS. 2-4 illustrate an electrosurgical system 10A having a handle assembly 208. In a first embodiment shown by FIG. 2, the handle assembly 208 is provided therein with a motor 210, similar to the embodiment shown by FIG. 1B. The motor 210 can be a high speed motor as known in the art. The motor 210 is in operative communication with an eccentric weight 212 positioned at a distal end of an ablation probe 214.

The eccentric weight 212 is mechanically connected to the motor 210 via a mechanical linkage assembly 216 designed to transfer mechanical vibration energy from the motor 210 through a longitudinal member 213, such as a shaft or cooling jacket, of the probe 214 to the eccentric weight 212. The linkage assembly 216 can include one or more rigid rods. The mechanical vibration energy causes the eccentric weight 212 to vibrate, and thereby impart vibrational energy to a distal end 211 of the ablation probe 214. The vibrational energy causes the ablation probe 214, especially its distal end 211, to vibrate, and thereby increase the ultrasonic visibility of the probe 214. The handle assembly 208 can include one or more controls 217 for operating the ablation probe 214 of the electrosurgical system, including actuating the motor 210 or other vibrating device during ultrasonography.

The motor 210 can also be on the handle assembly 208 as shown by FIG. 3, similar to positioning the motor 210 on the hub 142 as shown by FIG. 1A. When the motor 210 is positioned on the handle assembly 208, an eccentric weight 212A can be connected thereto via a mechanical connection 219, such as at least one rigid rod. Activation of the motor 210 transfers mechanical vibration energy via a longitudinal member 213, such as a shaft or cooling jacket, of the probe 214 to the distal end 211 of the probe 214. The mechanical vibration energy causes the distal end 211 of the ablation probe 214 to vibrate, and thereby increase the ultrasonic visibility of the probe 214. A vibrating distal end of the ablation probe 214 has greater ultrasonic visibility than a non-vibrating distal end.

Variations of the above described mechanical vibration embodiments include using the controls 217 or a controller, such as a processor. to perform at least one of the following: adjusting the speed of the motor or other vibrating device to determine the resonant frequency of the energy-delivery devices 100, 214, and adjusting the speed of the motor 210 to determine the harmonic frequency of the ultrasonic imaging system in operative communication with the electrosurgical system.

It is contemplated that the electrosurgical systems can include a controller, such as a processor, for performing at least two or more of the mechanical vibrating actions described above for vibrating the energy-delivery device, such as, for example, rapidly varying or sweeping the frequency to allow the energy-delivery device to continually pass through the resonant frequency of the energy-delivery device or harmonic frequency of the ultrasonic imaging system used for performing ultrasonography.

In embodiments, vibration of the energy-delivery device can be achieved by the use of other vibrating devices, besides a motor, capable of generating mechanical vibrational energy, such as micro-machines, IC chip, electromagnet, etc.

In the embodiments of the electrosurgical system 10 shown in FIGS. 1A and 1B, a processor unit 82 is disposed within or otherwise associated with the electrosurgical power generating source 28. Processor unit 82 may be communicatively-coupled to one or more components or modules of the electrosurgical power generating source 28, e.g., a user interface 121 and a generator module 86. Processor unit 82 may additionally, or alternatively, be communicatively-coupled to one or more temperature sensors (e.g., two sensors "$TS_1$" and "$TS_2$" shown in FIGS. 1A and 1B) and/or one or more flow sensors (e.g., one sensor "$FS_1$" shown in FIGS. 1A and 1B) for receiving one or more signals indicative of a temperature (referred to herein as temperature data) and/or one or more signals indicative of a flow rate (referred to herein as flow data). Transmission lines may be provided to electrically couple the temperature sensors, flow sensors and/or other sensors, e.g., pressure sensors, to the processor unit 82.

Electrosurgical power generating source 28 may include any generator suitable for use with electrosurgical devices, and may be configured to provide various frequencies of electromagnetic energy. In some embodiments, the electrosurgical power generating source 28 is configured to provide microwave energy at an operational frequency from about 300 MHz to about 10 GHz. In some embodiments, the electrosurgical power generating source 28 is configured to provide electrosurgical energy at an operational frequency from about 400 KHz to about 500 KHz.

Probe 100 may include one or more antennas of any suitable type, such as an antenna assembly (or antenna array) suitable for use in tissue ablation applications. For ease of explanation and understanding, the probe 100 is described as including a single antenna assembly 112. In some embodiments, the antenna assembly 112 is substantially disposed within a sheath 138. Probe 100 generally includes a coolant chamber 137 defined about the antenna assembly 112. In some embodiments, the coolant chamber 137 includes an interior lumen defined by the sheath 138.

Probe 100 may include a feedline 110 coupled to the antenna assembly 112. A transmission line 16 may be provided to electrically couple the feedline 110 to the electrosurgical power generating source 28. Feedline 110 may be coupled to a connection hub 142, which is described in more detail later in this description, to facilitate the flow of coolant and/or buffering fluid into, and out of, the probe 100.

In the embodiments shown in FIGS. 1A and 1B and in accordance with the present disclosure, the feedback control system 14 is operably associated with a flow-control device 50 disposed in fluid communication with a fluid flow path of the coolant supply system 11 (e.g., first coolant path 19) fluidly-coupled to the probe 100. Flow-control device 50 may include any suitable device capable of regulating or controlling the rate of fluid flow passing though the flow-control device 50, or selectively blocking the fluid flow, e.g., a valve of any suitable type operable to selectively impede or restrict flow of fluid through passages in the valve, for among other purposes, causing hydraulic energy in the form of high pressure pulses to be transferred or transmitted to the ablation probe 100.

The hydraulic energy is transferred or transmitted via the fluid flow path thorough the ablation probe 100 causing the ablation probe 100 to vibrate. The vibration of the ablation probe 100 enhances its ultrasonic visibility. It is envisioned that one or more additional flow-control devices can be positioned at different locations along the fluid flow path, including on the ablation probe 100, for selectively blocking and unblocking the fluid flow for transferring hydraulic energy to the ablation probe 100, especially to tapered portion 120 of the ablation probe 100. The hydraulic energy causes vibration of the ablation probe 100 which enhances its ultrasonic visibility.

In embodiments, the flow-control device 50 may include a valve 52 having a valve body 54 and an electromechanical actuator 56 operatively-coupled to the valve body 54. Valve body 54 may be implemented as a ball valve, gate valve, butterfly valve, plug valve, or any other suitable type of valve. In the embodiments shown in FIGS. 1A and 1B, the actuator 56 is communicatively-coupled to with the processor unit 82 via a transmission line 32. Processor unit 82 may be configured to control the flow-control device 50 by activating the actuator 56 to selectively block fluid flow, or adjust the fluid flow rate in a fluid flow path (e.g., first coolant path 19 of the coolant supply system 11) fluidly-coupled to the connection hub 142 to achieve a desired fluid flow rate. The amount of time the fluid flow is blocked or the desired fluid flow rate may be determined by a computer program and/or logic circuitry associated with the processor unit 82. The amount of time the fluid flow is blocked or the desired fluid flow rate may additionally, or alternatively, be selected from a look-up table or determined by a computer algorithm.

In other embodiments according to the present disclosure, controls can be used to control the speed of a pump for creating high pressure pulses to be transferred or transmitted to the ablation probe 100. For example, a multi-speed pump can be provided on the fluid flow path, similar to fluid-movement device 60 described further below, instead of a valve, and the processor unit 82 may be configured to vary the pump speed to selectively adjust the fluid flow rate to attain a desired fluid flow rate, and to selectively turn on and off the pump.

At higher pumping speeds, the fluid pressure of the circulating cooling fluid through the energy-delivery device is increased, thereby causing increased vibration of the energy-delivery device 100. The speed of the pump can also be adjusted to determine the resonant frequency of the energy-delivery device 100 or the harmonic frequency of the ultrasonic imaging system performing the ultrasonography.

In another embodiment of the present disclosure, the electrosurgical system 10 includes a pulsating device in operative communication with the pump. The pulsating device rapidly alternates the direction of fluid flow for achieving maximum hydraulic pressure change within the energy-delivery device 100 and vibration of the energy-delivery device 100. The vibration of the energy-delivery device 100 enhances the ultrasonic visibility of the energy-delivery device 100.

In still another embodiment of the present disclosure, the electrosurgical system 10 performs at least two or more of the hydraulic vibrating actions described above for vibrating the energy-delivery device 100, such as, for example, blocking the fluid flow while a controller, such as a processor, rapidly varies or sweeps the frequency to allow the energy-delivery device 100 to continually pass through the resonant frequency (or harmonic frequency) of the ultrasonic imaging system.

Processor unit 82 may also be configured to control the flow-control device 50 based on determination of a desired fluid flow rate using temperature data received from one or more temperature sensors (e.g., "$TS_1$" and "$TS_2$").

With continued reference to FIGS. 1A and 1B, electrosurgical system 10 includes a suitable pressure-relief device 40 disposed in fluid communication with the diversion flow path 21 which may allow the fluid-movement device 60 to run at a substantially constant speed and/or under a near-constant load (head pressure) regardless of the selective adjustment of the fluid flow rate in the first coolant path 19. Utilizing the suitable pressure-relief device 40 disposed in fluid communication with the diversion flow path 21, in accordance with the present disclosure, may allow the fluid-movement device 60 to be implemented as a single speed device, e.g., a single speed pump.

Feedback control system 14 may utilize data "D" (e.g., data representative of a mapping of temperature data to settings for properly adjusting one or more operational parameters of the flow-control device 50 to achieve a desired temperature and/or a desired ablation) stored in a look-up table, or other data structure, to determine the desired fluid flow rate. In the embodiments shown in FIGS. 1A and 1B, the electrosurgical system 10 includes a first temperature sensor "$TS_1$" capable of generating a signal indicative of a temperature of a medium in contact therewith and a second temperature sensor "$TS_2$" capable of generating a signal indicative of a temperature of a medium in contact therewith. Feedback control system 14 may be configured to utilize signals received from the first temperature sensor "$TS_1$" and/or the second temperature sensor "$TS_2$" to control the flow-control device 50.

In some embodiments, the electrosurgical system 10 includes a flow sensor "$FS_1$" communicatively-coupled to the processor unit 82, e.g., via a transmission line 36. In some embodiments, the flow sensor "$FS_1$" may be disposed in fluid communication with the first coolant path 19 or the second coolant path 20. Processor unit 82 may be configured to control the flow-control device 50 based on determination of a desired fluid flow rate using one or more signals received from the flow sensor "$FS_1$". In some embodiments, the processor unit 82 may be configured to control the flow-control device 50 based on determination of a desired fluid flow rate using one or more signals received from the flow sensor "$FS_1$" in conjunction with one or more signals received from the first temperature sensor "$TS_1$" and/or the second temperature sensor "$TS_2$". Although the electrosurgical system 10 shown in FIGS. 1A and 1B includes one flow sensor "$FS_1$", alternative embodiments may be implemented with a plurality of flow sensors adapted to provide a measurement of the rate of fluid flow into and/or out of the probe 100 and/or conduit fluidly-coupled to the probe 100.

Electrosurgical system 10 may additionally, or alternatively, include one or more pressure sensors adapted to provide a measurement of the fluid pressure in the probe 100 and/or conduit fluidly-coupled the probe 100. In some embodiments, the electrosurgical system 10 includes one or more pressure sensors (e.g., pressure sensor 70) disposed in fluid communication with one or more fluid flow paths (e.g., first coolant path 19) of the coolant supply system 11 as opposed to a pressure sensor disposed within the probe 100, reducing cost and complexity of the probe 100.

In the embodiments shown in FIGS. 1A and 1B, the processor unit 82 is operably associated with a pressure sensor 70 disposed in fluid communication with a fluid flow path of the coolant supply system 11. Processor unit 82 may be communicatively-coupled to the pressure sensor 70 via a transmission line 30 or wireless link. Processor unit 82 may additionally, or alternatively, be operably associated with one or more pressure sensors disposed within the probe 100, e.g., disposed in fluid communication with the coolant chamber 137, for monitoring the fluid flow pressure within the probe 100.

Pressure sensor 70 may include any suitable type of pressure sensor, pressure transducer, pressure transmitter, or pressure switch. Pressure sensor 70 (also referred to herein as "pressure transducer") may include a variety of components, e.g., resistive elements, capacitive elements and/or piezoresistive elements, and may be disposed at any suitable position in the coolant supply system 11. In some embodiments, the pressure transducer 70 is disposed in fluid communication with the first coolant path 19 located between the fluid-movement device 60 and the flow-control device 50, e.g., placed at or near the flow-control device 50.

In some embodiments, the processor unit 82 may be configured to control the flow-control device 50, and/or other valve controlling fluid flow for transferring hydraulic energy to the ablation probe 100, based on determination of a desired fluid flow rate using pressure data received from one or more pressure sensors and/or vibration data received from one or more accelerometers 232. The one or more accelerometers can be positioned at a distal end of the probe 100 as shown by FIGS. 1A and 1B.

In some embodiments, the processor unit 82 may be configured to control the flow-control device 50 based on determination of a desired fluid flow rate using one or more signals received from the first temperature sensor "$TS_1$" and/or the second temperature sensor "$TS_2$" and/or the flow sensor "$FS_1$" in conjunction with one or more signals received from the pressure transducer 70 and/or one or more accelerometers 232. The one or more accelerometers may be positioned on the probe 100 for monitoring the amount of vibration or displacement of the probe 100 from its axis, such as its longitudinal axis.

In some embodiments, the processor unit 82 may be configured to control the amount of power delivered to the antenna assembly 112 based on time and power settings provided by the user in conjunction with sensed temperature signals indicative of a temperature of a medium, e.g., coolant fluid "F", in contact with one or one temperature sensors operably associated with the antenna assembly 112 and/or the connection hub 142. In some embodiments, the processor unit 82 may be configured to decrease the amount of power delivered to the antenna assembly 112 when sensed temperature signals indicative of a temperature below a predetermined temperature threshold are received by processor unit 82, e.g., over a predetermined time interval.

Processor unit 82 may be configured to control one or more operating parameters associated with the electrosurgical power generating source 28 based on determination of whether the pressure level of fluid in the probe 100 and/or conduit fluidly-coupled to the probe 100 is above a predetermined threshold using pressure data received from one or more pressure sensors, e.g., pressure transducer 70. Examples of operating parameters associated with the electrosurgical power generating source 28 include without limitation temperature, impedance, power, current, voltage, mode of operation, and duration of application of electromagnetic energy.

In some embodiments, the output signal of the pressure transducer 70, representing a pressure value and possibly amplified and/or conditioned by means of suitable components (not shown), is received by the processor unit 82 and used for determination of whether the pressure level of fluid in the probe 100 and/or conduit fluidly-coupled to the probe 100 is above a predetermined threshold in order to control when power is delivered to the antenna assembly 112. In some embodiments, in response to a determination that the pressure level of fluid in the probe 100 and/or conduit fluidly-coupled to the probe 100 is below the predetermined threshold, the processor unit 82 may be configured to decrease the amount of power delivered to the antenna assembly 112 and/or to stop energy delivery between the electrosurgical power generating source 28 and the probe 100. In some embodiments, the processor unit 82 may be configured to enable energy delivery between the electrosurgical power generating source 28 and the probe 100 based on determination that the pressure level of fluid in the probe 100 and/or conduit fluidly-coupled to the probe 100 is above the predetermined threshold.

In some embodiments, the pressure transducer 70 is adapted to output a predetermined signal to indicate a sensed pressure below that of the burst pressure of the pressure-relief device 40. A computer program and/or logic circuitry associated with the processor unit 82 may be configured to enable the electrosurgical power generating source 28 and the flow-control device 50 in response to a signal from the pressure transducer 70. A computer program and/or logic circuitry associated with the processor unit 82 may be configured to output a signal indicative of an error code and/or to activate an indicator unit 129 if a certain amount of time elapses between the point at which energy delivery to the probe 100 is enabled and when the pressure signal is detected, e.g., to ensure that the fluid-movement device 60 is turned on and/or that the probe 100 is receiving flow of fluid before the antenna assembly 112 can be activated.

As shown in FIGS. 1A and 1B, a feedline 110 couples the antenna assembly 112 to a connection hub 142. Connection hub 142 may have a variety of suitable shapes, e.g., cylindrical, rectangular, etc. Connection hub 142 generally includes a hub body 145 defining an outlet fluid port 177 and an inlet fluid port 179. Hub body 145 may include one or more branches, e.g., three branches 164, 178 and 176, extending from one or more portions of the hub body 145. In some embodiments, one or more branches extending from the hub body 145 may be configured to house one or more connectors and/or ports, e.g., to facilitate the flow of coolant and/or buffering fluid into, and out of, the connection hub 142.

In the embodiments shown in FIGS. 1A and 1B, the hub body 145 includes a first branch 164 adapted to house a cable connector 165, a second branch 178 adapted to house the inlet fluid port 179, and a third branch 176 adapted to house the outlet fluid port 177. It is to be understood, however, that other connection hub embodiments may also be used. Examples of hub embodiments are disclosed in commonly assigned U.S. patent application Ser. No. 12/401,268 filed on Mar. 10, 2009, entitled "COOLED DIELECTRICALLY BUFFERED MICROWAVE DIPOLE ANTENNA", and U.S. Pat. No. 7,311,703, entitled "DEVICES AND METHODS FOR COOLING MICROWAVE ANTENNAS"; the contents of both are incorporated herein by reference.

In some embodiments, the flow sensor "$FS_1$" is disposed in fluid communication with the first coolant path 19, e.g., disposed within the inlet fluid port 179 or otherwise associated with the second branch 178, and the second temperature sensor "$TS_2$" is disposed in fluid communication with the second coolant path 20, e.g., disposed within the outlet fluid port 177 or otherwise associated with the third branch 176. In other embodiments, the second temperature sensor "$TS_2$" may be disposed within the inlet fluid port 179 or otherwise associated with the second branch 178, and the flow sensor "$FS_1$" may be disposed within the outlet fluid port 177 or otherwise associated with the third branch 176.

Coolant supply system 11 generally includes a substantially closed loop having a first coolant path 19 leading to the probe 100 and a second coolant path 20 leading from the probe 100, a coolant source 90, and the fluid-movement device 60, e.g., disposed in fluid communication with the first coolant path 19. In some embodiments, the coolant supply system 11 includes a third coolant path 21 (also referred to herein as a "diversion flow path") disposed in fluid communication with the first coolant path 19 and the second coolant path 20. The conduit layouts of the first coolant path 19, second coolant path 20 and third coolant path 21 may be varied from the configuration depicted in FIGS. 1A and 1B.

In some embodiments, a pressure-relief device 40 may be disposed in fluid communication with the diversion flow path 21. Pressure-relief device 40 may include any type of device, e.g., a spring-loaded pressure-relief valve, adapted to open at a predetermined set pressure and to flow a rated capacity at a specified over-pressure. In some embodiments, one or more flow-restrictor devices (not shown) suitable for preventing backflow of fluid into the first coolant path 19 may be disposed in fluid communication with the diversion flow path 21. Flow-restrictor devices may include a check valve or any other suitable type of unidirectional flow restrictor or backflow preventer, and may be disposed at any suitable position in the diversion flow path 21 to prevent backflow of fluid from the diversion flow path 21 into the first coolant path 19.

In some embodiments, the first coolant path 19 includes a first coolant supply line 66 leading from the coolant source 90 to the fluid-movement device 60, a second coolant supply line 67 leading from the fluid-movement device 60 to the flow-control device 50, and a third coolant supply line 68 leading from the flow-control device 50 to the inlet fluid port 179 defined in the second branch 178 of the connection hub body 145, and the second coolant path 20 includes a first coolant return line 95 leading from the outlet fluid port 177 defined in the third branch 176 of the hub body 145 to the coolant source 90. Embodiments including the diversion flow path 21 may include a second coolant return line 94 fluidly-coupled to the second coolant supply line 67 and the first coolant return line 95. Pressure-relief device 40 may be disposed at any suitable position in the second coolant return line 94. The spacing and relative dimensions of coolant supply lines and coolant return lines may be varied from the configuration depicted in FIGS. 1A and 1B.

Coolant source 90 may be any suitable housing containing a reservoir of coolant fluid "F". Coolant fluid "F" may be any suitable fluid that can be used for cooling or buffering the probe 100, e.g., deionized water, or other suitable cooling medium. Coolant fluid "F" may have dielectric properties and may provide dielectric impedance buffering for the antenna assembly 112. Coolant fluid "F" may be a conductive fluid, such as a saline solution, which may be delivered to the target tissue, e.g., to decrease impedance and allow increased power to be delivered to the target tissue. A coolant fluid "F" composition may vary depending upon desired cooling rates and the desired tissue impedance matching properties. Various fluids may be used, e.g., liquids including, but not limited to, water, saline, perfluorocarbon, such as the commercially available Fluorinert® perfluorocarbon liquid offered by Minnesota Mining and Manufacturing Company (3M), liquid chlorodifluoromethane, etc. In other variations, gases (such as nitrous oxide, nitrogen, carbon dioxide, etc.) may also be utilized as the cooling fluid. In yet another variation, a combination of liquids and/or gases, including, for example, those mentioned above, may be utilized as the coolant fluid "F".

In the embodiments shown in FIGS. 1A and 1B, the fluid-movement device 60 is provided in the first coolant path 19 to move the coolant fluid "F" through the first coolant path 19 and into, and out of, the probe 100. Fluid-movement device 60 may include valves, pumps, power units, actuators, fittings, manifolds, etc. The position of the fluid-movement device 60, e.g., in relation to the coolant source 90, may be varied from the configuration depicted in FIGS. 1A and 1B. Although the coolant supply system 11 shown in FIGS. 1A and 1B includes a single, fluid-movement device 60 located in the first coolant path 19, various combinations of different numbers of fluid-movement devices, variedly-sized and variedly-spaced apart from each other, may be provided in the first coolant path 19 and/or the second coolant path 20.

In some embodiments, the probe 100 includes a feedline 110 that couples the antenna assembly 112 to a hub, e.g., connection hub 142, that provides electrical and/or coolant connections to the probe 100. Feedline 110 may be formed from a suitable flexible, semi-rigid or rigid microwave conductive cable. Feedline 110 may be constructed of a variety of electrically-conductive materials, e.g., copper, gold, or other conductive metals with similar conductivity values. Feedline 110 may be made of stainless steel, which generally offers the strength required to puncture tissue and/or skin.

In some variations, the antenna assembly 112 includes a distal radiating portion 105 and a proximal radiating portion 140. In some embodiments, a junction member (not shown), which is generally made of a dielectric material, couples the proximal radiating section 140 and the distal radiating section 105. In some embodiments, the distal and proximal radiating sections 105, 140 align at the junction member and are also supported by an inner conductor (not shown) that extends at least partially through the distal radiating section 105.

Antenna assembly 112 or probe 214 may be provided with an end cap or tapered portion 120, which may terminate in a sharp tip 123 to allow for insertion into tissue with minimal resistance. One example of a straight probe with a sharp tip that may be suitable for use is commercially available under the trademark EVIDENT™ offered by Covidien. The end cap or tapered portion 120 may include other shapes, such as, for example, a tip 123 that is rounded, flat, square, hexagonal, or cylindroconical. End cap or tapered portion 120 may be formed of a material having a high dielectric constant, and may be a trocar.

Sheath 138 generally includes an outer jacket 139 defining a lumen into which the antenna assembly 112, or portion thereof, may be positioned. In some embodiments, the sheath 138 is disposed over and encloses the feedline 110, the proximal radiating portion 140 and the distal radiating portion 105, and may at least partially enclose the end cap or tapered portion 120. The outer jacket 139 may be formed of any suitable material, such as, for example, polymeric or ceramic materials. The outer jacket 139 may be a water-cooled catheter formed of a material having low electrical conductivity.

In accordance with the embodiments shown in FIGS. 1A and 1B, a coolant chamber 137 is defined by the outer jacket 139 and the end cap or tapered portion 120. Coolant chamber 137 is disposed in fluid communication with the inlet fluid port 179 and the outlet fluid port 177 and adapted to circulate coolant fluid "F" therethrough, and may include baffles, multiple lumens, flow restricting devices, or other structures that may redirect, concentrate, or disperse flow depending on their shape. Examples of coolant chamber embodiments are disclosed in commonly assigned U.S. patent application Ser. No. 12/350,292 filed on Jan. 8, 2009, entitled "CHOKED DIELECTRIC LOADED TIP DIPOLE MICROWAVE ANTENNA", commonly assigned U.S. patent application Ser. No. 12/401,268 filed on Mar. 10, 2009, entitled "COOLED DIELECTRICALLY BUFFERED MICROWAVE DIPOLE ANTENNA", and U.S. Pat. No. 7,311,703, entitled "DEVICES AND METHODS FOR COOLING MICROWAVE ANTENNAS", the contents of these references are incorporated herein by reference. The size and shape of the sheath 138 and the coolant chamber 137 extending therethrough may be varied from the configuration depicted in FIGS. 1A and 1B.

During microwave ablation, e.g., using the electrosurgical system 10, the probe 100 is inserted into or placed adjacent to tissue and microwave energy is supplied thereto. Ultrasonography is used to accurately guide the probe 100 into the area of tissue to be treated in accordance with the present disclosure. Probe 100 may be placed percutaneously or atop tissue, e.g., using conventional surgical techniques by surgical staff. A clinician may pre-determine the length of time that microwave energy is to be applied. Application duration may depend on many factors such as tumor size and location and whether the tumor was a secondary or primary cancer. The duration of microwave energy application using the probe 100 may depend on the progress of the heat distribution within the tissue area that is to be destroyed and/or the surrounding tissue. Single or multiple probes 100 may be used to provide ablations in short procedure times, e.g., a few seconds to minutes, to destroy cancerous cells in the target tissue region.

A plurality of probes 100 may be placed in variously arranged configurations to substantially simultaneously ablate a target tissue region, making faster procedures possible. Multiple probes 100 can be used to synergistically create a large ablation or to ablate separate sites simultaneously. Tissue ablation size and geometry is influenced by a variety of factors, such as the energy applicator design, number of energy applicators used simultaneously, time and wattage.

In operation, microwave energy having a wavelength, lambda ($\lambda$), is transmitted through the antenna assembly 112, e.g., along the proximal and distal radiating portions 140, 105, and radiated into the surrounding medium, e.g., tissue. The length of the antenna for efficient radiation may be dependent on the effective wavelength $\lambda_{\mathit{eff}}$ which is dependent upon the dielectric properties of the medium being radiated. Antenna assembly 112, through which microwave energy is transmitted at a wavelength $\lambda$, may have differing effective wavelengths $\lambda_{\mathit{eff}}$ depending upon the surrounding medium, e.g., liver tissue as opposed to breast tissue.

In some embodiments, the electrosurgical system 10 includes a first temperature sensor "$TS_1$" disposed within a distal radiating portion 105 of the antenna assembly 112. First temperature sensor "$TS_1$" may be disposed within or contacting the end cap or tapered portion 120. It is to be understood that the first temperature sensor "$TS_1$" may be disposed at any suitable position to allow for the sensing of temperature. Processor unit 82 may be electrically connected by a transmission line 34 to the first temperature sensor "$TS_1$". Sensed temperature signals indicative of a temperature of a medium in contact with the first temperature sensor "$TS_1$" may be utilized by the processor unit 82 to control the flow of electrosurgical energy and/or the flow rate of coolant to attain the desired ablation.

Electrosurgical system 10 may additionally, or alternatively, include a second temperature sensor "$TS_2$" disposed within the outlet fluid port 177 or otherwise associated with the third branch 176 of the hub body 145. Processor unit 82 may be electrically connected by a transmission line 38 to the second temperature sensor "$TS_2$". First temperature sensor "$TS_1$" and/or the second temperature sensor "$TS_2$" may be a thermocouple, thermistor, or other temperature sensing device. A plurality of sensors may be utilized including units extending outside the tip 123 to measure temperatures at various locations in the proximity of the tip 123.

As described in U.S. patent application Ser. No. 13/043, 694, which is commonly-owned, a memory device in operable connection with the processor unit 82 can be provided. In some embodiments, the memory device may be associated with the electrosurgical power generating source 28. The memory device may also be implemented as a storage device integrated into the electrosurgical power generating source 28. In some embodiments, the memory device may be implemented as an external device communicatively-coupled to the electrosurgical power generating source 28.

The processor unit 82 may be communicatively-coupled to the flow-control device 50, e.g., via a transmission line, and may be communicatively-coupled to the fluid-movement device 60, e.g., via a transmission line. In some embodiments, the processor unit 82 may be configured to control one or more operational parameters of the fluid-movement device 60 to selectively adjust the fluid flow rate in a fluid flow path (e.g., first coolant path 19) of the coolant supply system 11. In one non-limiting example, the fluid-movement device 60 is implemented as a multi-speed pump, and the processor unit 82 may be configured to vary the pump speed to selectively adjust the fluid flow rate to attain a desired fluid flow rate.

Processor unit 82 may be configured to execute a series of instructions to control one or more operational parameters of the flow-control device 50 based on determination of a desired fluid flow rate using temperature data received from one or more temperature sensors, e.g., "$TS_1$" and "$TS_2$". The temperature data may be transmitted via transmission lines or wirelessly transmitted. One or more flow sensors may additionally, or alternatively, be communicatively-coupled to the processor unit 82, e.g., via transmission lines. In some embodiments, signals indicative of the rate of fluid flow into and/or out of the probe 100 and/or conduit fluidly-coupled the probe 100 received from one or more flow sensors may be used by the processor unit 82 to determine a desired fluid flow rate. In such embodiments, flow data may be used by the processor unit 82 in conjunction with temperature data, or independently of temperature data, to determine a desired fluid flow rate. The desired fluid flow rate may be selected from a look-up table or determined by a computer algorithm stored within the memory device.

In some embodiments, an analog signal that is proportional to the temperature detected by a temperature sensor, e.g., a thermocouple, may be taken as a voltage input that can be compared to a look-up table for temperature and fluid flow rate, and a computer program and/or logic circuitry associated with the processor unit 82 may be used to determine the needed duty cycle of the pulse width modulation (PWM) to control actuation of a valve (e.g., valve 52) to attain the desired fluid flow rate. Processor unit 82 may be configured to execute a series of instructions such that the flow-control device 50 and the fluid-movement device 60 are cooperatively controlled by the processor unit 82, e.g., based on determination of a desired fluid flow rate using temperature data and/or flow data, to selectively adjust the fluid flow rate in a fluid flow path (e.g., first coolant path 19) of the coolant supply system 11.

Feedback control system 14 may be adapted to control the flow-control device 50 to allow flow (e.g., valve 52 held open) for longer periods of time as the sensed temperature rises, and shorter periods of time as the sensed temperature falls. Electrosurgical system 10 may be adapted to override PWM control of the flow-control device 50 to hold the valve 52 open upon initial activation of the antenna assembly 112. For this purpose, a timer may be utilized to prevent the control device 50 from operating for a predetermined time interval (e.g., about one minute) after the antenna assembly 112 has been activated. In some embodiments, the predetermined time interval to override PWM control of the flow-control device 50 may be varied depending on setting, e.g., time and power settings, provided by the user. In some embodiments, the electrosurgical power generating source 28 may be adapted to perform a self-check routine that includes determination that the flow-control device 50 is open before enabling energy delivery between the electrosurgical power generating source 28 and the probe 100.

In embodiments, features described for the electrosurgical system 10 having energy-delivery device 100 may be provided to an electrosurgical system having a handle assembly, as the handle assembly 208 shown by FIGS. 2-4. Other embodiments described herein below with reference to energy-delivery device 214 can be provided to energy-delivery device 100 of the system 10 shown by FIGS. 1A and 1B, and vice versa. Still other embodiments of the present disclosure for increasing or enhancing the ultrasonic visibility of an energy-delivery device will be described with reference to FIGS. 4-9.

With reference to FIG. 4, there is shown an embodiment of the present disclosure where ultrasonic visibility of the energy-delivery device 214 of an electrosurgical system within tissue is enhanced by providing an air cavity or pocket 222 at or near the distal end 211 of the energy-delivery device 214, such as, for example, before the tip of an ablation probe (as shown in FIG. 4), RF electrode or microwave antenna. The air cavity 222 is defined by a ring groove 224. However, it is contemplated that the cavity 222 can be of any shape or configuration.

With continued reference to FIG. 4, the ring groove 224 is circumferentially positioned around the energy-delivery device 214. The air cavity or pocket 222 can be created when heat shrink is placed over the top of the energy-delivery device 214. The air cavity 222 enhances ultrasonic visibility of the energy-delivery device 214 during placement, since air has a very high ultrasonic contrast compared to the surrounding tissue because of the difference in density and acoustic properties.

Figure 5:
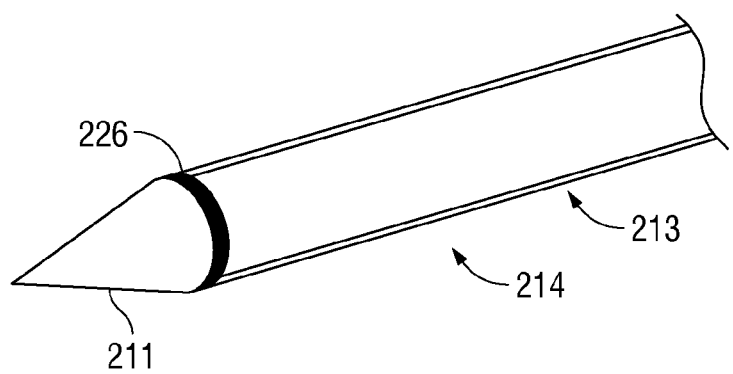
FIG. 5 is a schematic diagram of an electrosurgical system having a handle assembly and an energy-delivery device with a metal band in accordance with an embodiment of the present disclosure.

With reference to FIG. 5, there is shown an embodiment for enhancing ultrasonic visibility of the energy-delivery device 214 within tissue by positioning a metal band 226 to the energy-delivery device 214, such as, for example, positioning a metal band, either fixedly or removably positioned, on the shaft 213 extending from the handle assembly 208, at a distal end of an ablation probe or needle. The metal band 226 can also be located between a trocar at a distal end 211 of an ablation assembly and a cooling jacket. The metal band 226 can be provided with small dimples to further enhance the ultrasonic visibility of the energy-delivery device. The metal band 226 reflects the ultrasonic waves generated during ultrasonography and thereby, increases the ultrasonic visibility of the energy-delivery device 214.

Figure 6:
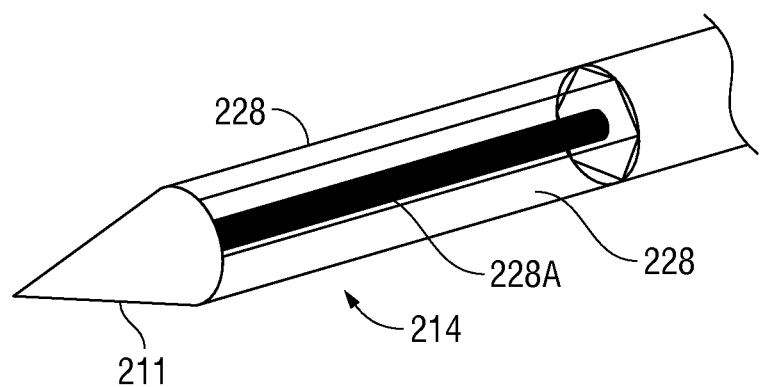
FIG. 6 is a schematic diagram of an electrosurgical system having a handle assembly and an energy-delivery device having a multi-sided distal end in accordance with an embodiment of the present disclosure.

With reference to FIG. 6, there is shown still another embodiment for enhancing or increasing the ultrasonic visibility of the energy-delivery device 214 within tissue. In this particular embodiment, the shape of a cooling jacket or shaft 213 of the energy-delivery device 214 is multi-sided, instead of circular, such as, for example, hexagonal. The outer surface of the cooling jacket or shaft 213 can be made multi-sided at or near the region of the radiating section of the energy-delivery device 214, such as at or near the distal end 211 of an ablation probe. The flat or substantially flat sides 228 of the cooling jacket or shaft 213 reflect the ultrasonic waves during ultrasonography, and thereby, enhance the ultrasonic visibility of the energy-delivery device 214. The surface of at least one side 228A can be made concave and/or be provided with small dimples to further enhance the ultrasonic visibility of the energy-delivery device 214.

Figure 7:
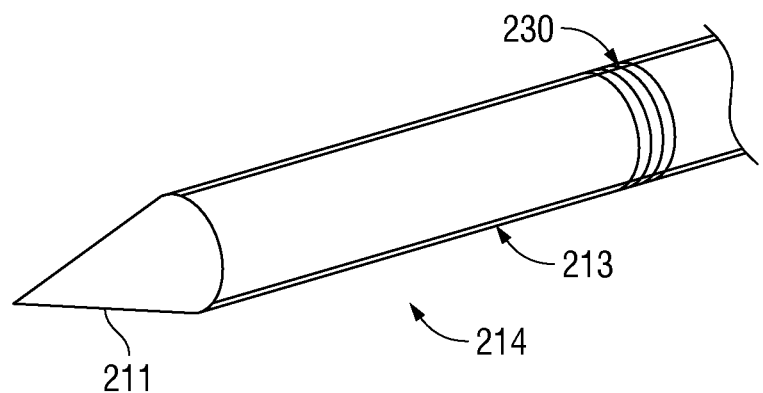
FIG. 7 is a schematic diagram of an electrosurgical system having a handle assembly and an energy-delivery device having a wire wrapped around an outer surface of the energy-delivery device in accordance with an embodiment of the present disclosure.

FIG. 7 illustrates a yet another embodiment of increasing or enhancing the ultrasonic visibility of the energy-delivery device 214 within tissue. In this embodiment, the cooling jacket or shaft 213 of the energy-delivery device 214 is provided with multiple metallic wires or one metallic wire which is coiled around the cooling jacket or shaft 213. The wires 230 can be individual loops or wrapped in the form of a coil or spring. The wires 230 are placed proximal to a radiating section of the energy-delivery device 214 in order to aid in identifying the start of the radiating section without interfering with the emitted energy, such as microwave energy. The wires 230 can also be placed over the active area of the radiating section in the case of an RF electrode, such as, a Cool-Tip™ electrode. The wires 230 reflect the ultrasonic waves generated during ultrasonography and thereby, increasing the ultrasonic visibility of the energy-delivery device 214.

Figure 8:
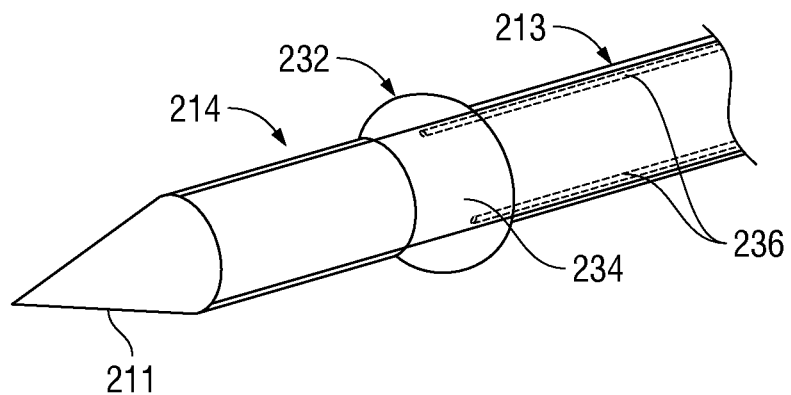
FIG. 8 is a schematic diagram of an electrosurgical system having a handle assembly and an energy-delivery device having an inflatable balloon in accordance with an embodiment of the present disclosure.

FIG. 8 shows another embodiment for enhancing the ultrasonic visibility of the energy-delivery device 214 within tissue. In this embodiment, ultrasonic visibility is enhanced by utilizing an inflatable balloon or air sac assembly 232. The assembly 232 includes an inflatable air sac or balloon 234 and at least one conduit 236 in fluid communication with a fluid source (not shown) for delivering and withdrawing fluid (liquid, gas, gel, etc.) to the air sac 234. The air sac 234 and the at least one conduit 236 are positioned along the shaft 213. By delivering fluid to the air sac 234, the air sac 234 inflates.

The fluid is delivered to the air sac 234 via the at least one conduit 236 when ultrasonic visibility of the energy-delivery device 214 is desired. It is also contemplated that the fluid is delivered to chamber positioned within the chamber, such as an inner chamber. In one configuration, the fluid is added between a cooling jacket and an outermost heat shrink, such as a PET heat shrink, during ultrasonography.

If a liquid is used as the fluid, the ultrasonic energy is absorbed and the liquid appears darker in contrast compared to surrounding tissue. If air is used as the fluid, the ultrasonic energy is reflected and the air appears brighter in contrast compared to surrounding tissue. The fluid can be added during guidance, positioning and placement of the energy-delivery device 214 within tissue, and be removed during the ablation procedure. The sac or balloon 234 can be positioned in the area proximal to a radiating section or on the radiating section of the energy-delivery device 214. The sac 234 can be in fluid communication with cooling fluid, such that the cooling fluid is used to inflate the sac 234.

In an additional embodiment, ultrasonic visibility of the energy-delivery device 214 within tissue is enhanced by increasing ultrasound reflection at or near the distal end 211 of the energy-delivery device 214, such as, for example, at a trocar 238. The ultrasound reflection can be increased at the distal end 211 by creating a concave surface 240 at the distal end 211 and/or adding a plurality of dimples 242 to the surface of the distal end. Ultrasonic visibility is also increased by making the trocar 238 multi-sided.

The distal end 211 can be made from ceramic material which is molded to have a concave surface and/or a plurality of dimples thereon. The concave surface and/or plurality of dimples increase the amount of ultrasonic energy which is reflected by the energy-delivery device 214, thereby enhancing its ultrasonic visibility. The dimples can also be added on a cooling jacket, shaft, heat shrink or other structure of the energy-delivery device 214.

Figure 9:
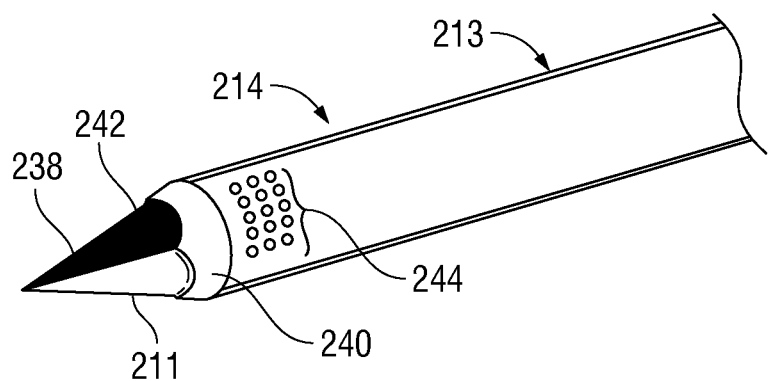
FIG. 9 is a schematic diagram of an electrosurgical system having a handle assembly and an energy-delivery device having a multi-sided trocar and protrusions at a distal end in accordance with an embodiment of the present disclosure.

In yet another embodiment, with continued reference to FIG. 9, ultrasonic visibility of the energy-delivery device 214 within tissue is enhanced by adding micro spheres or protrusions of a hard material 244, such as, ceramic, glass, stainless steel, etc., at or near the radiating section or a distal end 211 of the energy-delivery device 214. The micro spheres or protrusions 244 can also be added on a cooling jacket, shaft, heat shrink or other structure of the energy-delivery device 214.

The above-described methods and systems for enhancing ultrasonic visibility of energy-delivery devices or other components of electrosurgical systems may be used in conjunction with a variety of electrosurgical devices adapted for treating tissue. The above-described systems and methods may be suitable for a variety of uses and applications, including medical procedures, e.g., tissue ablation, resection, cautery, vascular thrombosis, treatment of cardiac arrhythmias and dysrhythmias, electrosurgery, etc.

It is envisioned that various aspects and features of the embodiments shown by the various figures and/or described herein can be combined to form additional embodiments of the electrosurgical system 10. For example, probe 100 of electrosurgical system 10 can be provided with an air cavity at a distal end and/or a metal band as shown by the embodiments of FIGS. 4 and 5, respectively.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method for increasing ultrasonic visibility of an energy-delivery device of an electrosurgical system, the method comprising:
    inserting an energy-delivery device within tissue, the energy-delivery device including at least one accelerometer disposed at a distal end of the energy-delivery device;
    circulating a fluid through the energy-delivery device;
    vibrating the energy-delivery device such that the ultrasonic visibility of the energy-delivery device is increased;
    determining a desired flow rate of the fluid flowing through the energy-delivery device based on vibration data received from the at least one accelerometer;
    actuating a vibrating device that is in mechanical communication with the energy-delivery device; and
    at least one of:
        adjusting a vibration frequency of the vibrating device to determine a resonant frequency of the energy-delivery device; or
        sweeping a frequency of the vibrating device.

2. The method according to claim 1, wherein the vibrating device is a motor.

3. The method according to claim 1, further comprising controlling the fluid flow based on the determined desired flow rate.

4. The method according to claim 1, further comprising forming bubbles at the distal end of the energy-delivery device to enhance ultrasonic visibility of the energy-delivery device.

5. The method according to claim 1, wherein the energy-delivery device includes an air cavity defined therein.

6. The method according to claim 1, wherein the energy-delivery device includes a metal band.

7. The method according to claim 1, wherein the energy-delivery device includes an outer surface, the outer surface including at least one of:
    a plurality of sides;
    a plurality of protrusions; or
    a concave surface.

8. The method according to claim 1, wherein the energy-delivery device is selected from the group consisting of an electrode, a probe, and an antenna.

9. A method for increasing ultrasonic visibility of an energy-delivery device of an electrosurgical system, the method comprising:
    inserting an energy-delivery device within tissue, the energy-delivery device including at least one accelerometer disposed at a distal end of the energy-delivery device;
    circulating a fluid through the energy-delivery device;
    vibrating the energy-delivery device such that the ultrasonic visibility of the energy-delivery device is increased;
    determining a desired flow rate of the fluid flowing through the energy-delivery device based on vibration data received from the at least one accelerometer;
    actuating a vibrating device that is in mechanical communication with the energy-delivery device; and
    adjusting a vibration frequency of the vibrating device to determine a harmonic frequency of an ultrasonic imaging device that is in operative communication with the energy-delivery device.

10. A method for increasing ultrasonic visibility of an energy-delivery device of an electrosurgical system, the method comprising:
    inserting an energy-delivery device within tissue, the energy-delivery device including at least one accelerometer disposed at a distal end of the energy-delivery device, the energy-delivery device including at least one of:
        an air cavity defined therein; or
        a metal band;
    circulating a fluid through the energy-delivery device;
    vibrating the energy-delivery device such that the ultrasonic visibility of the energy-delivery device is increased; and
    determining a desired flow rate of the fluid flowing through the energy-delivery device based on vibration data received from the at least one accelerometer.

* * * * *